(12) United States Patent
Rush et al.

(10) Patent No.: US 8,936,611 B2
(45) Date of Patent: Jan. 20, 2015

(54) APPARATUS AND METHODS FOR ACHILLES TENDON REPAIR

(75) Inventors: Shannon M. Rush, Pleasanton, CA (US); Sheriese Rush, Pleasanton, CA (US)

(73) Assignee: Raptor Surgical, LLC, Pleasanton, CA (US)

( * ) Notice: Subject to any disclaimer, the term of this patent is extended or adjusted under 35 U.S.C. 154(b) by 850 days.

(21) Appl. No.: 13/113,505

(22) Filed: May 23, 2011

(65) Prior Publication Data

US 2011/0313454 A1    Dec. 22, 2011

Related U.S. Application Data

(60) Provisional application No. 61/349,025, filed on May 27, 2010.

(51) Int. Cl.
| | |
|---|---|
| *A61B 17/04* | (2006.01) |
| *A61B 17/062* | (2006.01) |
| *A61B 17/06* | (2006.01) |
| *A61B 17/00* | (2006.01) |

(52) U.S. Cl.
CPC .......... *A61B 17/062* (2013.01); *A61B 17/0466* (2013.01); *A61B 17/0482* (2013.01); *A61B 17/0485* (2013.01); *A61B 17/06066* (2013.01); *A61B 2017/00349* (2013.01); *A61B 2017/047* (2013.01); *A61B 2017/0472* (2013.01); *A61B 2017/06042* (2013.01); *A61B 2017/06052* (2013.01)
USPC ........................................... 606/144

(58) Field of Classification Search
CPC ................. A61B 17/0485; A61B 2017/00349; A61B 2017/047; A61B 2017/0472; A61B 2017/06042; A61B 2017/06052
USPC ......................................... 606/139, 144–148
See application file for complete search history.

(56) References Cited

U.S. PATENT DOCUMENTS

| | | | |
|---|---|---|---|
| 1,577,054 A | 3/1926 | Berkmann | |
| 2,264,679 A | 12/1941 | Ravel | |
| 4,971,075 A | 11/1990 | Lee | |
| 5,397,325 A | 3/1995 | Della Badia et al. | |
| RE36,020 E | 12/1998 | Moore et al. | |
| 5,980,538 A | 11/1999 | Fuchs et al. | |
| 6,117,144 A * | 9/2000 | Nobles et al. | 606/144 |
| 6,746,456 B2 | 6/2004 | Xiao | |
| 6,921,408 B2 | 7/2005 | Sauer | |
| 7,758,597 B1 * | 7/2010 | Tran et al. | 606/144 |
| 2003/0181925 A1 * | 9/2003 | Bain et al. | 606/144 |
| 2007/0198037 A1 | 8/2007 | Deland | |
| 2009/0138029 A1 | 5/2009 | Saliman et al. | |
| 2009/0318958 A1 | 12/2009 | Ochiai | |

* cited by examiner

*Primary Examiner* — Gregory Anderson
(74) *Attorney, Agent, or Firm* — Levine Bagade Han LLP

(57) ABSTRACT

Apparatus and methods for Achilles tendon repair are described where an elongate tendon repair assembly may be introduced into a single incision to access the damaged tissue. The assembly may define a channel for receiving a portion of the tendon and which may provide support to the tissue during repair. One or more retractable needles each carrying a length of suture may be deployed within the channel for piercing through the tendon and a cinching member may secure each of the suture lengths for tensioning the suture against the damaged tendon. Once the suture lengths have been deployed, the needles may be retracted and the device removed from the incision.

32 Claims, 11 Drawing Sheets

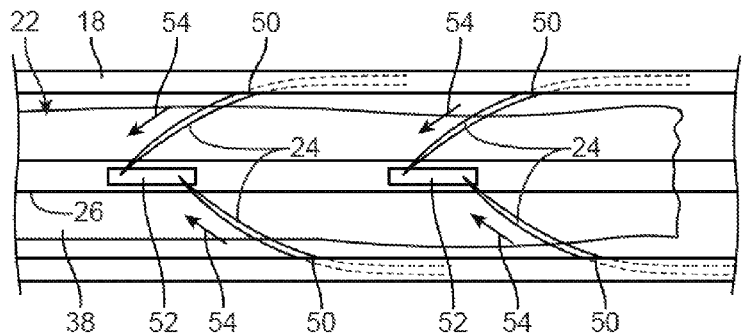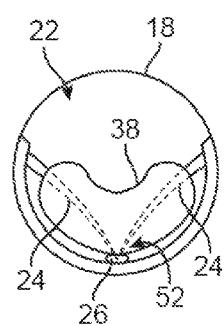
FIG. 4A  FIG. 4B
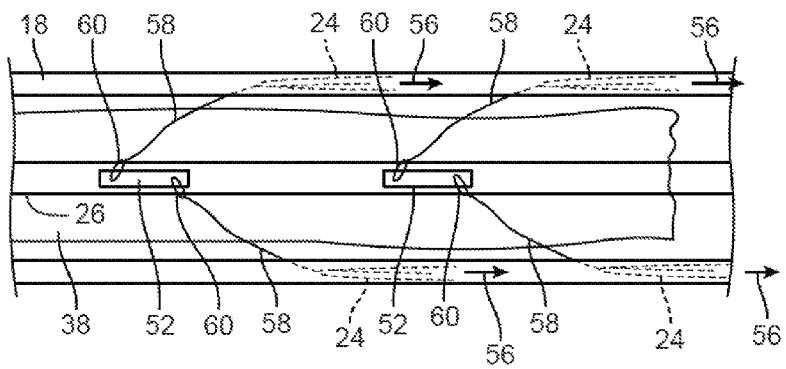
FIG. 4C
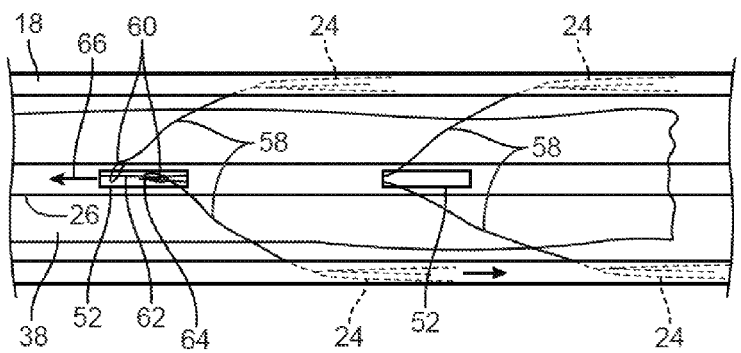
FIG. 4D

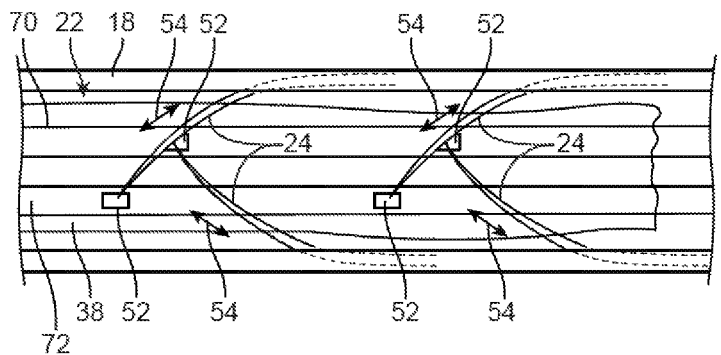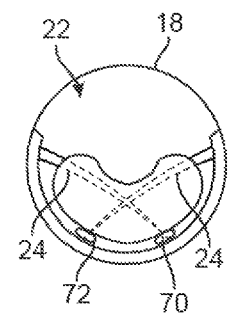
FIG. 5A  FIG. 5B
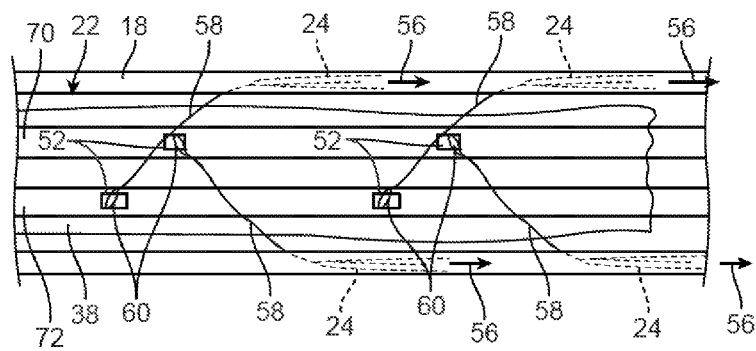
FIG. 5C
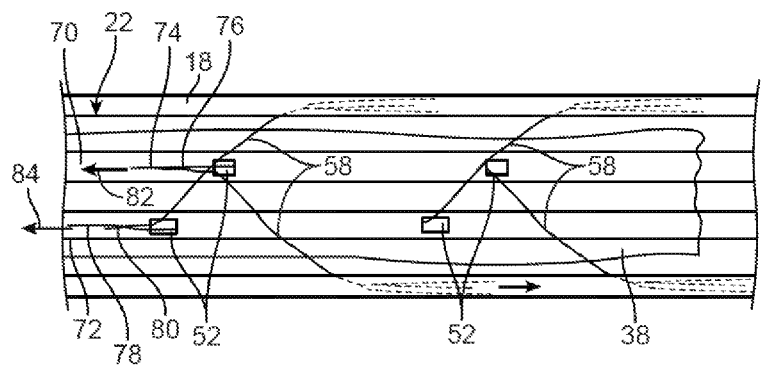
FIG. 5D

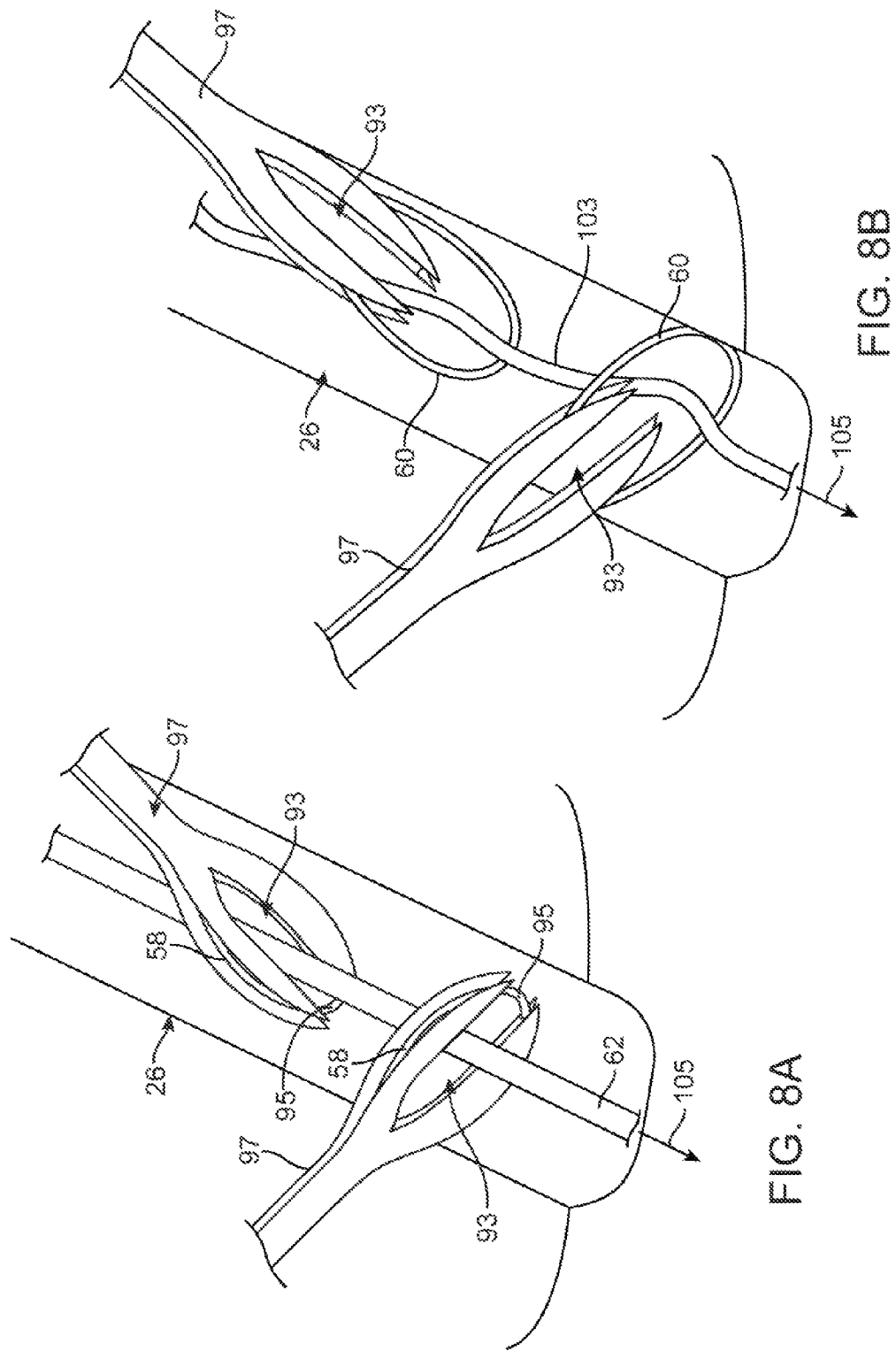

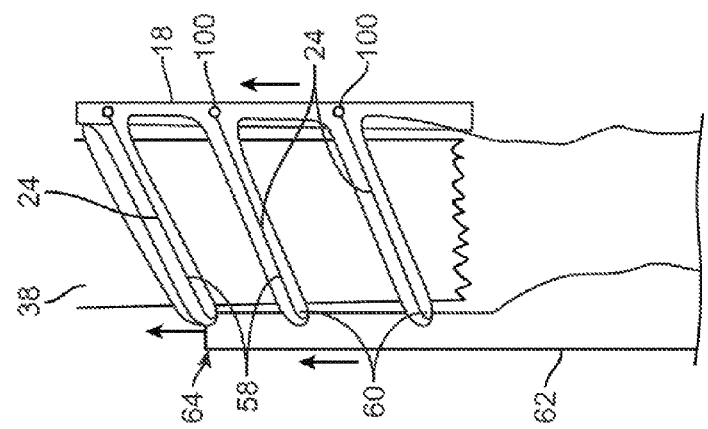
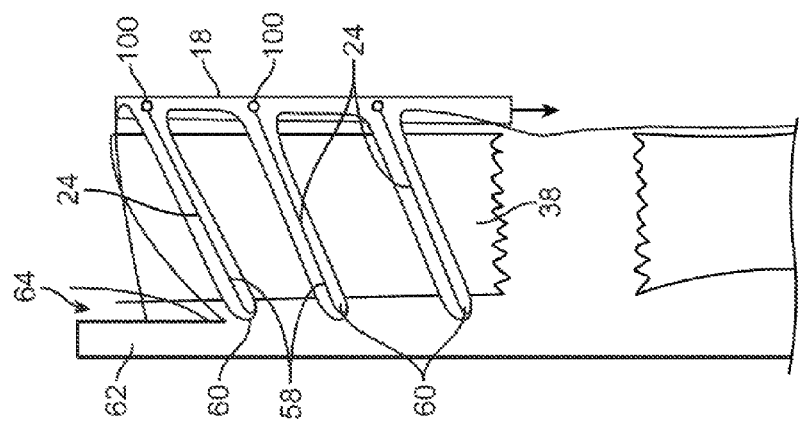
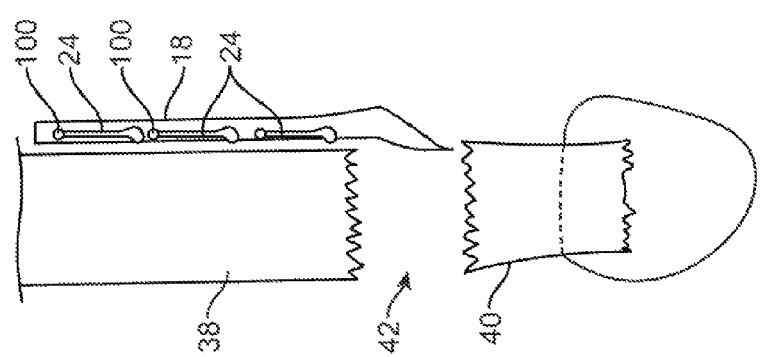

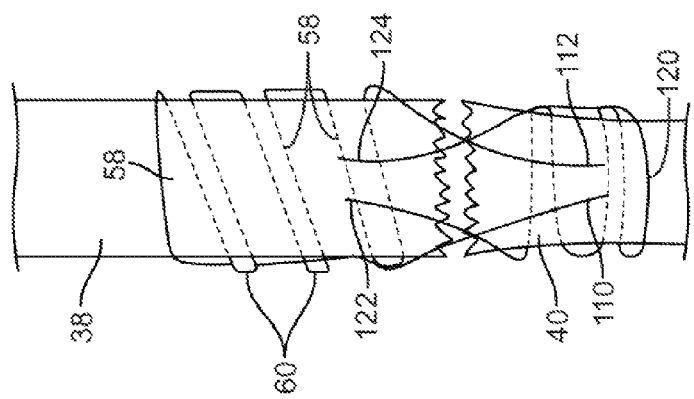
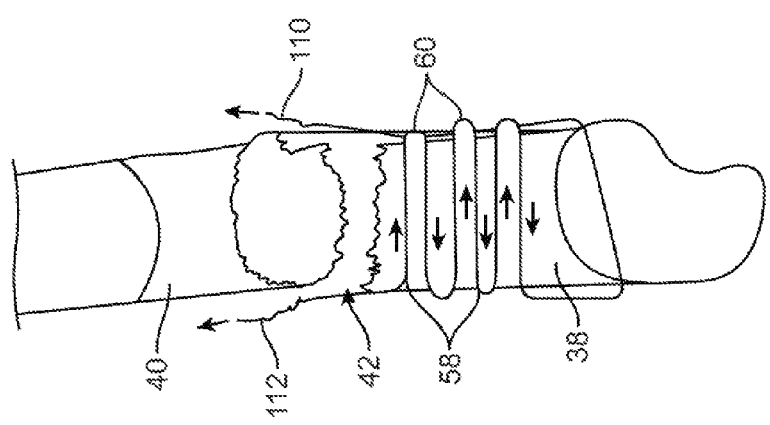
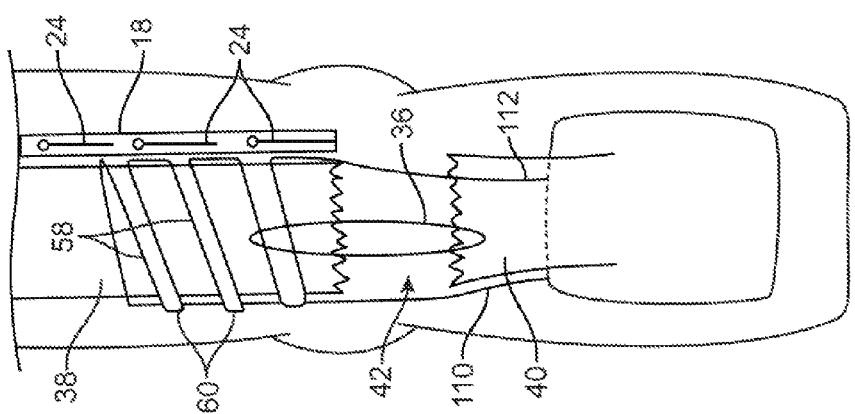

APPARATUS AND METHODS FOR ACHILLES TENDON REPAIR

CROSS-REFERENCE TO RELATED APPLICATIONS

This application claims the benefit of priority of U.S. Provisional Application No. 61/349,025, filed on May 27, 2010, the content of which is incorporated herein by reference in its entirety.

FIELD OF THE INVENTION

The present invention relates generally to medical devices and methods used for attaching soft tissues to one another. More particularly, the present invention relates to apparatus and methods for re-attaching a damaged tissue region to one another such as a ruptured Achilles tendon in a minimally invasive manner.

BACKGROUND OF THE INVENTION

Soft tissue damage, particularly tendon rupture such as the Achilles tendon, is typically a debilitating event. Surgical repair of a ruptured tendon generally requires the torn or ripped ends of the tendon, which are separated from one another, to be coapted by passing one or more sutures through each damaged end. Each of the torn ends are drawn towards one another by tightening of the sutures to restore the connecting muscles and tendon to their original lengths.

However, accessing the damaged tissue generally requires relatively large incisions or multiple smaller incisions for effecting adequate purchase and sufficient suturing of the damaged tendon to ensure proper healing of the tendon. Yet relatively large incisions or multiple incisions also increase the likelihood of infections and complications occurring.

Moreover, minimally invasive devices which may be inserted through relatively smaller incisions are generally limited in their application for repairing particular tissue regions. For instance, minimally invasive surgical instruments may enable a surgeon to pass sutures through tissue with the instruments introduced through relatively small incisions; however, these instruments are limited in their ability to pass multiple sutures through non-supported tissue structures in an efficacious manner.

Moreover, may such devices are insufficient in supporting tissue structures such as ruptured or torn tendons for minimally invasive surgical repair. Thus, tissue repair systems which are able to pass one or more sutures in a minimally invasive manner into tissue structures, such as the Achilles tendons, which are difficult to secure and manipulate are highly desirable.

BRIEF SUMMARY OF THE INVENTION

In repairing damaged regions of tissue, an elongate assembly may be introduced into a single incision to access damaged tissue such as a ruptured or torn Achilles tendon. Thus, a tendon repair assembly may generally comprise an elongate body which allows for insertion of the instrument through a relatively small incision into proximity of the damaged tendon. The assembly may comprise a channel for receiving a portion of the tendon and which may provide support to the tissue during repair. Although described in reference to the suturing and repair of tendons, particularly the Achilles tendon, the devices and methods described herein may be utilized on other tissue regions.

An example of a tendon repair assembly may generally comprise a handle housing having a handle grip and an actuator operable relative to the housing. An elongate shaft may extend from the housing and terminate with a distal end which may be rounded or atraumatic to prevent damage to surrounding tissues when the elongate shaft is introduced into the body of the patient. The length of the elongate shaft may extend to about 5 cm although the shaft may be lengthened or shortened as desired or necessary. Moreover, the shaft may have a circular cross-sectional shape ranging, e.g., between 2 to 2.5 cm in diameter, while in other variations the cross-sectional shape may be elliptical or another shape conducive for atraumatic insertion within the patient's body.

The elongate shaft may define a receiving channel which runs along at least a portion of the length of the shaft and is sized to allow for the damaged or ruptured tendon to be inserted or enclosed at least partially or completely within the channel. The opening of the channel may be sized sufficiently to allow for entry of the tendon within and may accordingly vary depending upon the application and size of the tendon. Typically, the channel may range anywhere from 45 degrees to 180 degrees relative to the circumference of the shaft but the opening may be less or greater depending on the application. Moreover, the channel may be defined along the shaft at an angle relative to an orientation of the handle. In one example, the grip of handle may be angled anywhere from about 45 degrees or greater, e.g., 90 degrees, about the longitudinal axis of the shaft relative to the opening of the channel. Having an angled orientation between the handle and the channel may allow for the insertion of the shaft into the posterior region of the patient's leg to access the Achilles tendon without any interference between the handle and the patient's foot or leg.

One or more needles which are retractably or pivotably extendable from a low profile configuration within the channel may be positioned within or along the walls of shaft such that when retracted, the needles may be flush or hidden within shaft and when extended, the needles may extend at least partially within channel in a deployed or extend configuration. Each of the needles may extend at an angle relative to the longitudinal axis of the shaft, e.g., anywhere from 15 degrees to 25 degrees or more, such that the needles extend angularly towards a single or multiple locking channels which extends along the shaft interior within channel. Each of the needles may be angled proximally towards the handle to facilitate securement of the needles through the tendon during a procedure such that the user may readily pull on the shaft while deploying the needles into the channel and into or through a tendon positioned within the channel while retracting the device to ensure securement to the tendon.

The shaft may be introduced through a single incision, e.g., 3 cm in length, which may be in proximity to the rupture between a first or superior portion of tendon and a second or inferior portion of the tendon such that the channel is oriented towards the damaged tendon. Because the handle assembly is angled relative to the channel, the grip may be angled away from the patient's foot and remain freely operable without interference.

Once the shaft has been introduced through the incision and into proximity to the ruptured tendon, a first portion of the ruptured tendon may be manipulated to lie at least partially or entirely within the channel. Once suitably positioned, the actuator on handle assembly may be gripped or otherwise manipulated to deploy the one or more needles to extend into the channel. Once the one or more needles have pierced entirely through the tendon and into their respective needle receiving channels, each of the needles may be actuated to retract proximally back into the shaft while leaving a length of suture which is interconnected with one another (or a single common length of suture) passing through the tendon such that each suture loop remains within each respective needle receiving channel. An elongate cinching member having a hook or grasping member at its distal end may be positioned within the locking channel such that the grasping member is initially positioned within a distal end of the locking channel. With the suture loops positioned within each needle receiving channel, the grasping member may then be tensioned or pulled proximally such that each of the suture loops are secured and tensioned proximally through the locking channel and through the assembly where the entire length of suture may be tensioned for tightening against the tendon.

Alternatively, a terminal end of the common length of suture may be secured to the grasping member such that when the cinching member is pulled proximally, the terminal suture end may be passed through each of the suture loops and pulled proximally through the assembly such that the terminal end may be tightened through each suture loop whereby a single common suture length is secured to the tendon.

In yet another example of a tendon repair assembly, one or more needles may be rotatably positioned along the shaft such that the needles may be rotated upon pivots to extend proximally towards the handle. With each needle having a length of suture positioned therethrough or therealong, the shaft may be pulled proximally to drive each of the angled needles into and through the tendon until the suture loops are passed through the tendon. A cinching member may then be pulled proximally relative to the shaft such that a terminal end of the suture length attached to the grasping member is passed through each of the suture loops.

Yet another variation of the tendon repair assembly may define a receiving channel with the one or more needles housed in an off-set needle housing. Another example may comprise a curved needle rotatably coupled to the shaft via a corresponding pivot supported upon pivoting members. When actuated, the one or more needles may rotate upon the corresponding pivot to pass through the tendon in a curved manner. Another example may comprise a curved needle extending away from the shaft.

BRIEF DESCRIPTION OF THE DRAWINGS

FIGS. 4A and 4B show bottom and partial cross-sectional end views, respectively, of a damaged segment of tendon having multiple lengths of suture passed through simultaneously or sequentially.

FIGS. 4C and 4D show bottom views of the tendon segment having multiple lengths of suture passed through by their respective needles and a cinching member for tightening each of the suture lengths.

FIGS. 5A and 5B show bottom and partial cross-sectional end views, respectively, of another variation where multiple lengths of suture may be passed through simultaneously or sequentially in a crossing pattern.

FIGS. 5C and 5D show bottom views of the tendon segment having multiple lengths of suture passed through in a crossing pattern.

FIGS. 8A and 8B show perspective views illustrating how the needle assembly may be positioned within or along the common locking channel such that the cinching member and cinching suture may be passed through the openings within each needle assembly subsequently allowing for the needle assemblies to be retracted while leaving the looped suture behind.

FIGS. 9A to 9C show posterior views of another variation of a tendon repair assembly having one or more needles which are pivotably deployable prior to advancement into or through the tendon for passing lengths of suture therethrough.

FIG. 10 shows a posterior view of the resulting suture lengths passed through a portion of the tendon prior to removal or repositioning of the assembly.

FIG. 11 shows a posterior view of the sutured tendon and the resulting securement of the suture to the tendon when tightened.

FIG. 12 shows a posterior view of the ruptured tendon having both complementary segments sutured via a repair assembly through a single incision for approximation and securement to one another.

DETAILED DESCRIPTION OF THE INVENTION

In repairing damaged regions of tissue, an elongate assembly may be introduced into a single incision to access the damaged tissue. Ruptured or torn tendons in particular may be difficult to repair due to the fibrous and relative toughness of these tissues. Additionally, ruptured or torn tendons may be unsupported within the body thus requiring the securement and approximation of the torn edges towards one another. Thus, a tendon repair assembly may generally comprise an elongate body which allows for insertion of the instrument through a relatively small incision into proximity of the damaged tendon. The assembly may comprise a channel for receiving a portion of the tendon and which may provide support to the tissue during repair. Although described in reference to the suturing and repair of tendons, particularly the Achilles tendon, the devices and methods described herein may be utilized on other tissue regions.

Figure 1A:
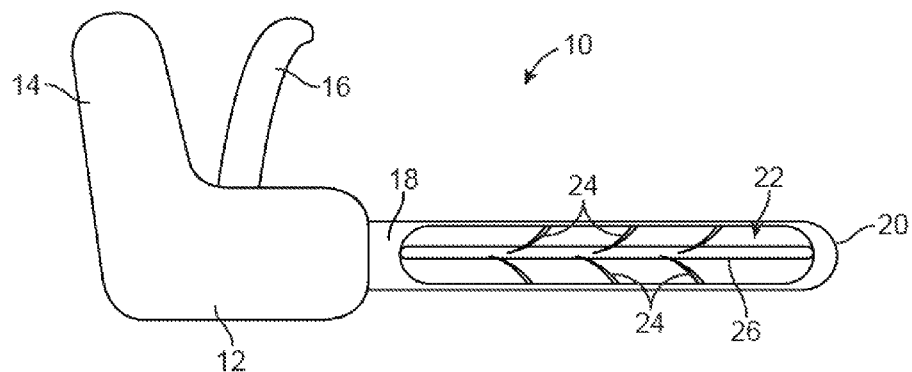
FIGS. 1A to 1C respectively show bottom, side, and partial cross-sectional end views of a tendon repair assembly which may be introduced into the body in a minimally invasive manner.
Figure 1B:
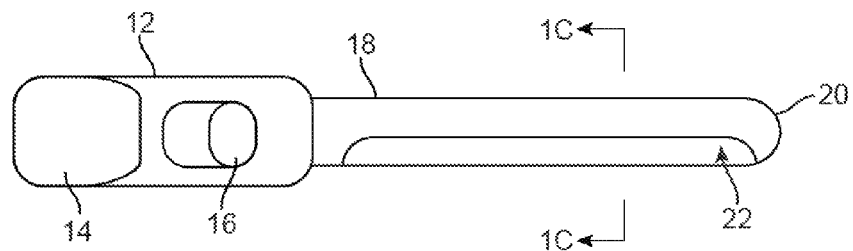

Turning now to the bottom and side views of FIGS. 1A and 1B, an example of a tendon repair assembly 10 is illustrated as having a handle housing 12 with a handle grip 14 and an actuator 16 operable relative to the housing 12. An elongate shaft 18 may extend from the housing 12 and terminate with a distal end 20 which may be rounded or atraumatic to prevent damage to surrounding tissues when the elongate shaft 18 is introduced into the body of the patient. The length of the elongate shaft 18 may extend to about 5 cm although the shaft may be lengthened or shortened as desired or necessary. Moreover, the shaft may have a circular cross-sectional shape ranging, e.g., between 2 to 2.5 cm in diameter, while in other variations the cross-sectional shape may be elliptical or another shape conducive for atraumatic insertion within the patient's body.

Figure 1C:
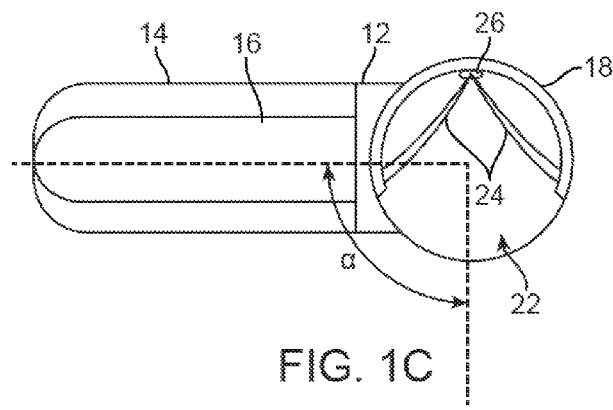

The elongate shaft 18 may define a receiving channel 22 which runs along at least a portion of the length of the shaft 18 and allows for the damaged or ruptured tendon to be inserted or enclosed at least partially or completely within the channel 22. The opening of the channel 22 may be sized sufficiently to allow for entry of the tendon within and may accordingly vary depending upon the application and size of the tendon. Typically, the channel 22 may range anywhere from 45 degrees to 180 degrees relative to the circumference of the shaft 18, as shown in the partial cross-sectional end view of FIG. 1C, but the opening may be less or greater depending on the application. Moreover, the channel 22 may be defined along the shaft 18 at an angle relative to an orientation of the handle 12. In one example, the grip 14 of handle 12 may be angled, α, anywhere from about 45 degrees or greater, e.g., 90 degrees, about the longitudinal axis of the shaft 18 relative to the opening of channel 22, as shown in FIG. 1C. Having an angled orientation between the handle 12 and the channel 22 may allow for the insertion of the shaft 18 into the posterior region of the patient's leg to access the Achilles tendon without any interference between the handle 12 and the patient's foot or leg.

One or more needles 24 which are retractably or pivotably extendable within channel 22 may be positioned within or along the walls of shaft 18 such that when retracted, the needles 24 may be flush or hidden within shaft 18 and when extended, needles 24 may extend at least partially within channel 22. Each of the needles 24 may extend at an angle relative to the longitudinal axis of the shaft 18, e.g., anywhere from 15 degrees to 25 degrees or more, such that the needles 24 extend angularly towards a common locking channel 26 which extends along the shaft 18 interior within channel 22, as shown in FIG. 1C. The needles 24 may be pre-formed to have a curve or arcuate shape or they may be comprised of a shape memory alloy such as a nickel-titanium alloy (e.g., Nitinol) whereby the needles may reconfigure from a straightened configuration to a curved configuration when deployed. Alternatively, the needles may be fabricated from a spring stainless steel which may curve when deployed as well. FIG. 1A illustrates at least three needles 24 on either side of channel 22 (for a total of six needles) and extending into channel 22 angled proximally towards handle 12 such that each needle 24 is offset relative to an adjacent needle 24. Each of the needles 24 may be angled proximally towards the handle 12 to facilitate securement of the needles 24 through the tendon during a procedure such that the user may readily pull on the shaft 18 while deploying the needles 24 into channel 22 and into or through a tendon positioned within the channel 22 while retracting the device to ensure securement to the tendon.

In other variations, each of the needles or alternating needles may be angled to extend into channel 22 at various angles relative to one another. Additionally, while six needles 24 are shown in this example, some variations may utilize fewer needles while other variations may utilize a greater number of needles. Moreover, with multiple needles 24 being deployed, each of the needles 24 may be deployed simultaneously when actuated or they may be deployed sequentially in a predetermined manner by varying the actuation mechanism for needle deployment.

Figure 2:
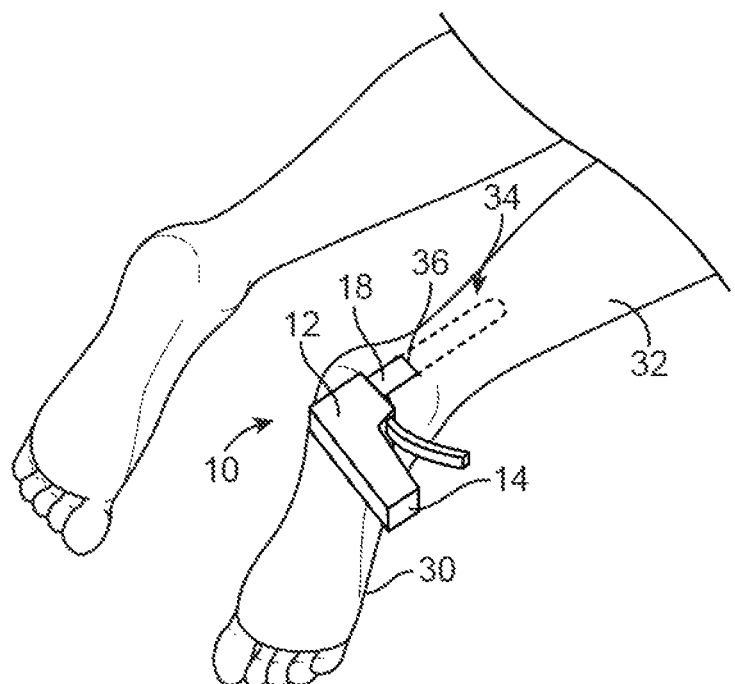
FIG. 2 shows a perspective view of an example for introducing the repair assembly through a single incision in proximity to the damaged tendon.
Figure 3:
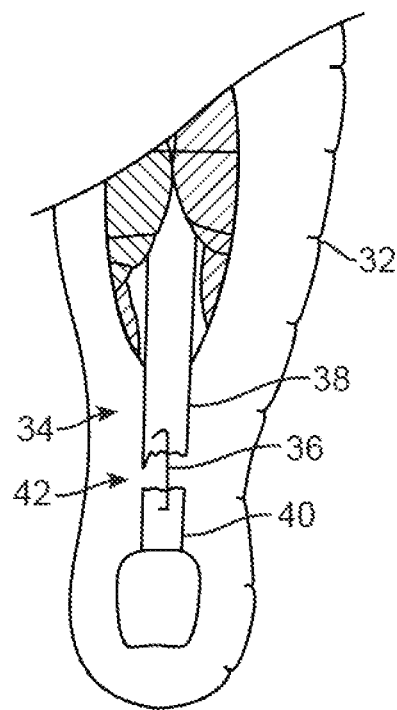
FIG. 3 shows a posterior view illustrating an incision through which the assembly may be introduced in proximity to the damaged tendon.

In an example of use, FIG. 2 illustrates a perspective view of an assembly 10 introduced into the posterior region of a patient's leg 32 superior to the foot 30 and in proximity to a ruptured or damaged tendon 34. As shown in both FIGS. 2 and 3 which illustrates a posterior view of a ruptured tendon 34, shaft 18 may be introduced through a single incision 36, e.g., 3 cm in length, which may be in proximity to the rupture 42 between a first or superior portion 38 of tendon 34 and a second or inferior portion 40 of tendon 34 such that the channel 22 is oriented towards the damaged tendon 34. Because the handle assembly 12 is angled relative to the channel 22, grip 14 may be angled away from the patient's foot 30 and remain freely operable without interference.

Once the shaft 18 has been introduced through the incision 36 and into proximity to the ruptured tendon 34, a first portion 38 of the ruptured tendon may be manipulated to lie at least partially or entirely within channel 22. Once suitably positioned, actuator 16 on handle assembly 12 may be gripped or otherwise manipulated to deploy the one or more needles 24 to extend into channel 22. As shown in the detail bottom view of FIG. 4A and the partial cross-sectional end view of FIG. 4B, the one or more needles 24 may extend through corresponding openings 50 defined along the interior of channel 22 from shaft 18 such that the needles 24 pierce into and through the tendon 38, as indicated by the direction of deployment 54, until the piercing tips of each needle 24 extend into a corresponding needle receiving channel 52 defined along the locking channel 26. The tendon 38 typically ranges in width from about 2 cm so the travel distance for a needle 24 passing through the tendon 38, as indicated in FIG. 4B, may range from about 1 to 1.5 cm for securement.

Once the one or more needles 24 have pierced entirely through the tendon 38 and into their respective needle receiving channels 52, each of the needles 24 may be actuated to retract proximally back into shaft 18, as indicated by the direction of retraction 56 shown in FIG. 4C. Each of the needles 24 may carry a length of suture which is interconnected with one another (or a single common length of suture) such that once the needles 24 are retracted, they may each leave a suture length 58 and a defined suture loop 60 passing through the tendon 38 such that each suture loop 60 remains within each respective needle receiving channel 52. An elongate cinching member 62 having a hook or grasping member 64 at its distal end may be positioned within the locking channel 26 such that the grasping member 64 is initially positioned within a distal end of the locking channel 26. With the suture loops 60 positioned within each needle receiving channel 52, the grasping member 64 may then be tensioned or pulled proximally, as indicated by the direction of cinching 66 shown in FIG. 4D, such that each of the suture loops 60 are secured and tensioned proximally through the locking channel 26 and through the assembly where the entire length of suture may be tensioned for tightening against the tendon 38.

Alternatively, a terminal end of the common length of suture may be secured to the grasping member 64 such that when the cinching member 62 is pulled proximally, the terminal suture end may be passed through each of the suture loops 60 and pulled proximally through the assembly such that the terminal end may be tightened through each suture loop 60 whereby a single common suture length is secured to the tendon 38.

FIGS. 5A and 5B show bottom and cross-sectional end views of another variation of the tendon repair assembly. In this example, rather than utilizing a single locking channel, a first locking channel 70 and a second locking channel 72 may be utilized where each of the channels 70, 72 are parallel and spaced apart from one another. In this manner, apposed needles 24 may extend from shaft 18 in a crossing manner when deployed, as shown in FIG. 5A. As described above, once the needles 24 have been passed into and through the tendon 38, as shown in FIG. 5B, and received into each respective needle receiving channel 52, the needles 24 may be retracted proximally while leaving each respective suture length 58 and suture loop 60 positioned within each channel 52, as shown in FIG. 5C. A first cinching member 74 having a first hook or grasping member 76 may be pulled proximally through the first locking channel 70, as indicated by the first member direction of cinching 82 and a second cinching member 78 having a second hook or grasping member 80 may also be pulled proximally through the second locking channel 72, as indicated by the second member direction of cinching 84, to cinch each of the suture loop 60 and to tighten the suture lengths against the tendon in a crossing manner, as shown in FIG. 5D.

Figure 6A:
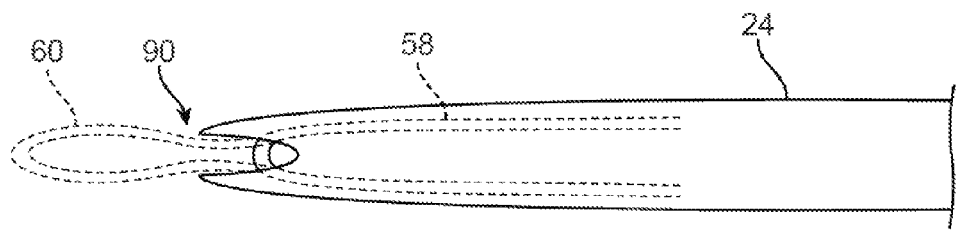
FIGS. 6A and 6B show side and cross-sectional side views of one example of the needle assemblies for delivering and deploying suture lengths through the tissue.
Figure 6B:
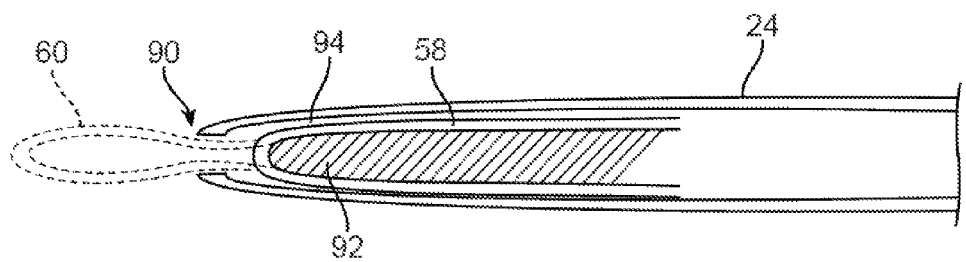

Turning now to the needles 24, each of the needles may have a piercing tip for passing through the tissue. A needle opening 90 may be defined at the piercing tip in communication with a suture lumen 94 defined through each needle. A length of the suture 58 may pass through the suture lumen 94 while resting against a suture abutment 92 such that during needle deployment, the suture 58 may readily pass through the tendon along with the needle travel. As the needle is retracted proximally, the suture 58 may have slack introduced into the length such that proximal movement of the needle 24 may urge the suture 58 through the suture lumen 94 and distally out through the needle opening 90 thus leaving a defined suture loop 60 extending from the suture length 58, as shown in the side and cross-sectional side views of FIGS. 6A and 6B. Alternatively, a pre-defined loop of suture may be formed at the distal end of suture length 58 such once deployed from the needle 24, the suture loop 60 may retain its looped shape once extended from the needle 24. Other variations for forming a suture loop may also be utilized with the tendon repair assembly described herein.

Figure 7A:
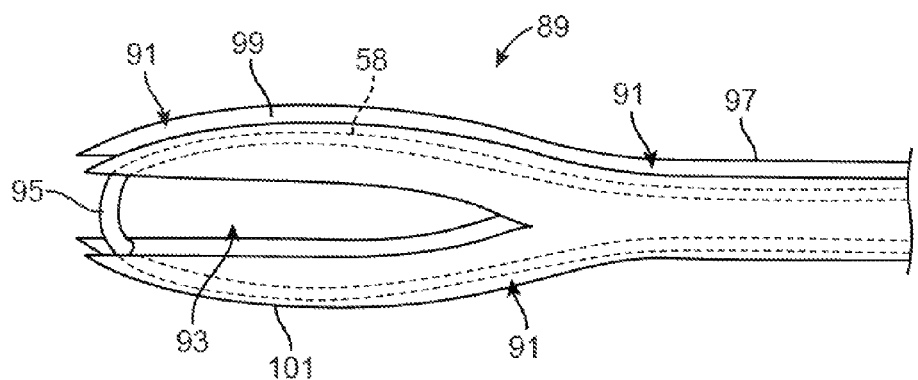
FIGS. 7A and 7B show perspective views of another example of the needle assembly which defines an open channel or groove for positioning of the suture length about an opening through which the cinching suture may be passed.
Figure 7B:
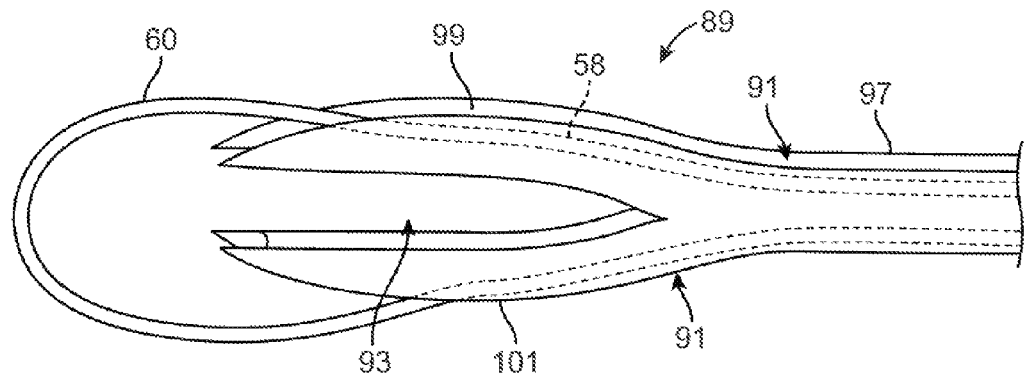

FIGS. 7A and 7B show perspective views of another example of a needle assembly 89 which is configured to allow for the passage and cinching of a cinching member and suture length directly through the needle assembly and defined suture loops. As shown, the suture length 58 may be a single suture which is slidably positioned within a channel 91 which is defined along either length of the needle body 97. In this example, channel 91 may be open along the entire length of the needle such that the suture length 58 remains open and is not enclosed or trapped within the needle itself. The distal end of the needle body 97 may comprise a first yoke member 99 and a second yoke member 101 which define an open passage 93 therebetween. A portion 95 of the suture length 58 may remain exposed between the distal tips of the first and second yoke members 99, 101 such that a cinching member or cinching suture passed through the open passage 93 may be released from between the yoke members 99, 101 and allow the suture length 58 to slide along the channels 91 such that the extended suture length 58 form a suture loop 60, as shown in FIG. 7B.

This particular design may allow for the needle assembly 89 to fully retract after each suture loop 60 has been threaded thus leaving the suture length 58 behind. As previously described, the open passage 93 may allow the grasping member or cinching suture to pull (or push) through each suture loop 60. Once the terminal end of the cinching suture is pulled external to the body and grasped by the user, the grasping member can be released back through the guide channel or pulled out entirely thus allowing for the needle assemblies 89 to be retracted leaving behind only the interlocking suture loops for cinching.

As further illustrated in FIGS. 8A and 8B, perspective views of the needle bodies 97 are shown deployed through the tendon and into the common locking channel 26, which may remain opened along its length, With the open passage 93 of each needle assembly linearly aligned within the locking channel 26, a grasping member 62 may be pushed or pulled through the length of the locking channel 26, as indicated by the direction 105. Because of the linear arrangement of the open passage 93 of each needle within the locking channel 26, the grasping member 62 may pass directly through each open passage 93, as shown in FIG. 8A. The grasping member 62 may be pulled or pushed through the device until the terminal end of the cinching suture 103 is urged through each open passage 93 by the grasping member 62 such that each suture loop 60 is accordingly retained by the cinching suture 103, as shown in FIG. 8B. Once the cinching suture 103 has been passed through each of the suture loops 60, the grasping member 62 may be removed from the device or retracted proximally through the locking channel 26 leaving only the cinching suture 103 locked through each suture loop 60. The needle body 97 may then be retracted proximally, as previously described, such that the cinching suture 103 passes through the open passage 93 and out between each of the yoke members 99, 101 while retaining each of the suture loops 60. The terminal end of the cinching suture 103, which may be drawn external to the patient's body, may then be tensioned and tightened by the user to secure each of the suture lengths 58 and cinching suture 103 to the tendon, as indicated by the direction 105 and as described herein.

In yet another example of a tendon repair assembly, FIGS. 9A to 9C illustrate a variation where one or more needles may be rotatably positioned along the shaft 18. As above, the shaft 18 may be introduced into proximity to the tendon to be repaired through a single incision in proximity to the rupture 42. In the example shown, shaft 18 may be advanced adjacent to the first portion of tendon 38 such that the needles 24 are positioned in proximity to the tendon surface, as shown in FIG. 9A. Each of the needles 24 may be rotated upon corresponding pivots 100 such that the needles 24 are angled to extend proximally towards the handle. With each needle 24 having a length of suture positioned therethrough or thereal-ong, the shaft 18 may be pulled proximally to drive each of the angled needles 24 into and through the tendon 38 until the suture loops 60 are passed through the tendon 38, as shown in FIG. 9B. A cinching member 62 may then be pulled proximally relative to the shaft 18 such that a terminal end of the suture length attached to the grasping member 64 is passed through each of the suture loops 60, as shown in FIG. 9C.

With the suture lengths 58 secured, shaft 18 may be advanced distally, as shown, until each of the needles 24 are cleared from the tendon 38 thus allowing the needles 24 to be retracted or angled back against the interior channel of shaft 18, as shown in FIG. 10. The resulting procedure may thus result in the tendon 38 having a single suture length secured to the tendon 38 with a first terminal suture end 110 and a second terminal suture end 112 extending from the tendon 38. FIG. 11 shows a superior view of the resulting tendon 38 having a single suture length secured thereto. One or both terminal suture ends 110, 112 may be tensioned, as shown, to draw the suture tightly against the tendon 38. The tendon repair assembly may then be withdrawn from the incision and re-inserted into (or simply re-oriented) the incision in an opposite direction to then secure a second length of suture 120 to the inferior portion of tendon 40 in the same or similar manner. The resulting procedure may result in the second length of suture 120 being secured to the second tendon 40 with a first terminal suture end 122 of the second suture 120 and a second terminal suture end 124 of the second suture 120, as shown in FIG. 12. Each of the terminal suture ends 110, 112 extending from the superior portion of tendon 38 and the terminal suture ends 122, 124 extending from the inferior portion of tendon 40 may then be drawn through the incision to coapt the ruptured portions of tendon against one another and tightened to secure the tendon for healing. The single incision may then be closed with minimal trauma to the patient.

Figure 13A:
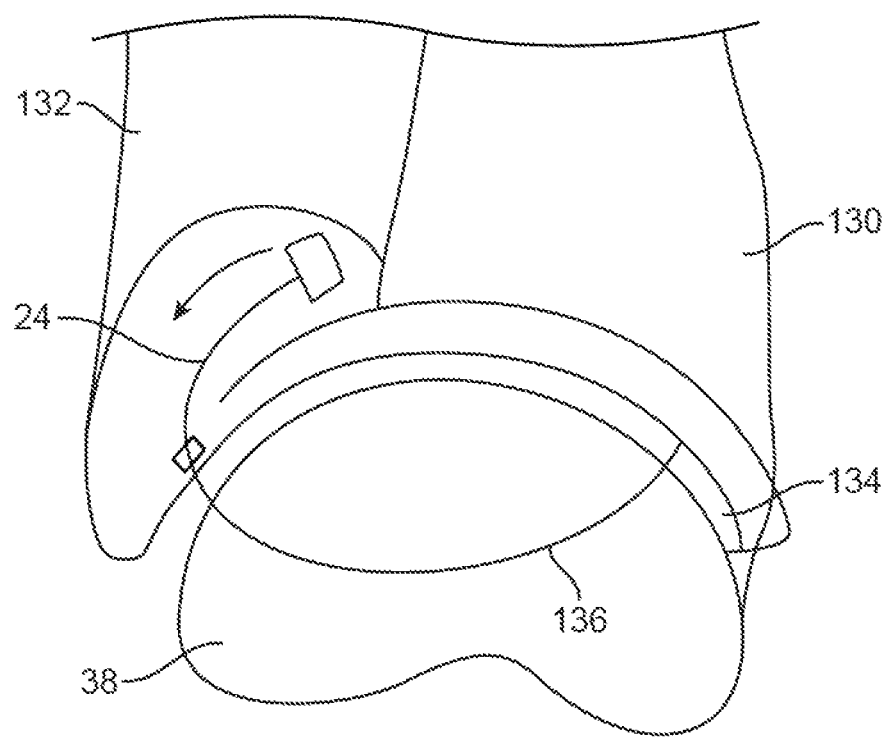
FIGS. 13A and 13B show perspective and end views, respectively, of another variation of the tendon repair assembly where the one or more needles may be deployed from an off-set portion of the elongate housing.
Figure 13B:
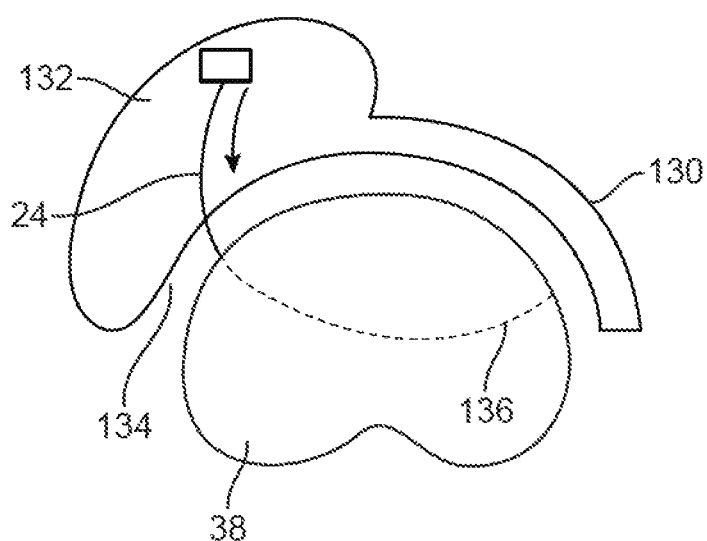

FIGS. 13A and 13B show perspective and end views of yet another variation of the tendon repair assembly. In this example, the elongate shaft 130 may define a receiving channel 134, as previously described, but the one or more needles 24 may be housed in an off-set needle housing 132. The needle housing 132 may project from shaft 130 and the one or more needles 24 may be curved such that when actuated, each of the needles may pass through the tendon in a curved or arcuate trajectory for passing the suture 136 therethrough.

Figure 14A:
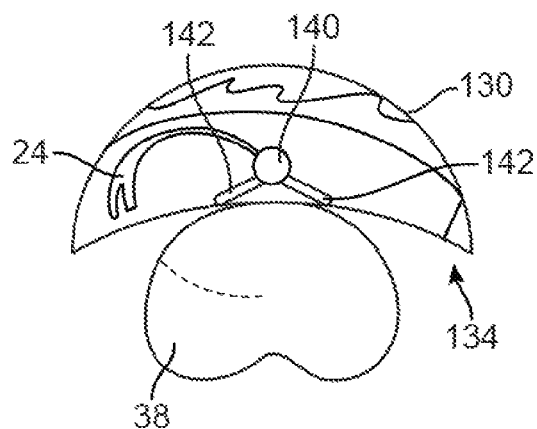
FIGS. 14A to 14C show end views of additional variations of the tendon repair assembly utilizing one or more curved needles which may rotate about a corresponding pivot for advancement into or through the tendon.
Figure 14B:
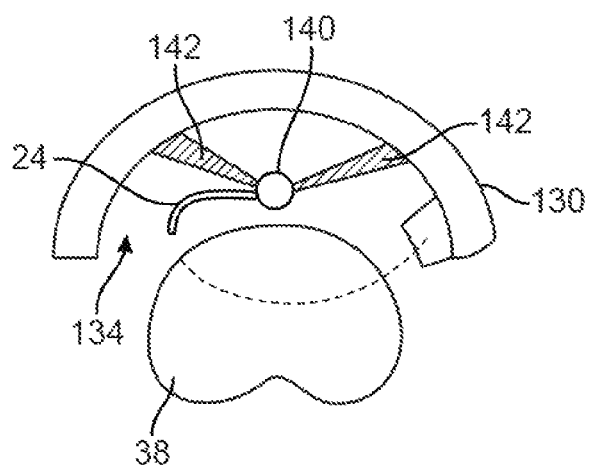
Figure 14C:
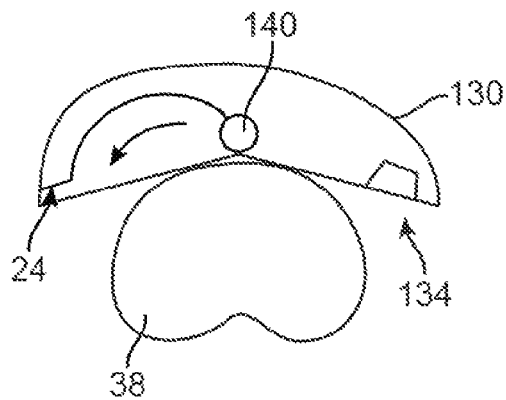

FIG. 14A shows yet another example where the curved needle 24 may be rotatably coupled to the shaft 130 via a corresponding pivot 140 supported upon pivoting members 142. When actuated, the one or more needles 24 may rotate upon the corresponding pivot 140 to pass through tendon 38 in a curved manner. FIG. 14B shows another example there the pivot 140 and curved needle 24 may extend away from the shaft 130 while FIG. 14C shows yet another example where the one or more needles 24 may be supported upon the shaft 130 and pivotably mounted via a corresponding pivot 140.

The applications of the disclosed invention discussed above are not limited to certain treatments or regions of the body, but may include any number of other treatments and areas of the body. Modification of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

What is claimed is:

1. A tissue repair assembly, comprising:
   a shaft defining an elongated channel therealong which is sized for receiving a length of tissue therein;
   one or more needles which are retractably extendable from a low-profile configuration within or along the channel to a deployed configuration where the one or more needles extend in an arcuate shape at least partially within the channel;
   one or more lengths of suture each defining a looped segment formed upon a portion of each of the one or more needles such that each looped segment is positioned along the one or more needles to be passed through the tissue;
   a locking channel positioned to receive each of the portions of the one or more needles in a corresponding manner such that each looped segment is aligned along the locking channel when in the deployed configuration and where the portions of the one or more needles are received at an angle relative to the locking channel; and,
   a cinching member slidably positioned within the locking channel such that actuation of the cinching member secures each looped segment of the one or more lengths of suture positioned within the locking channel.

2. The assembly of claim 1 wherein the shaft has a length of about 5 cm.

3. The assembly of claim 1 wherein the shaft has a diameter ranging from 2 cm to 2.5 cm.

4. The assembly of claim 1 wherein the elongated channel is sized for receiving an Achilles tendon.

5. The assembly of claim 1 further comprising a handle assembly attached to a proximal end of the shaft, where the handle assembly is oriented at an angle relative to the elongated channel.

6. The assembly of claim 1 wherein the one or more needles are configurable between a straightened configuration and a curved configuration when deployed.

7. The assembly of claim 1 wherein the one or more needles are off-set relative to one another.

8. The assembly of claim 1 wherein the one or more needles comprise at least three needles on each opposed side of the elongated channel.

9. The assembly of claim 1 wherein the one or more needles each comprise a suture lumen therethrough or therealong.

10. The assembly of claim 1 wherein the one or more lengths of suture comprise a single common length of suture.

11. The assembly of claim 1 wherein the one or more lengths of suture each define a suture loop extendable from a distal tip of the one or more needles.

12. The assembly of claim 1 wherein the cinching member comprises a grasping end which secures each of the one or more lengths of suture.

13. The assembly of claim 1 wherein the portion of each of the one or more needles defining the loop segment is positioned distally along the one or more needles.

14. The assembly of claim 1 wherein the needles are configured to extend into the elongated channel in the deployed configuration.

15. The assembly of claim 1 wherein the cinching member is actuated in a direction transverse to each loop segment.

16. The assembly of claim 1 wherein the cinching member is actuated in a direction parallel with the elongated channel.

17. A method for repairing tissue, comprising:
    introducing a shaft defining an elongated channel therealong in proximity to a ruptured or torn tissue;
    positioning a first portion of the ruptured or torn tissue within the elongated channel;
    actuating one or more needles from a low-profile configuration within or along the channel to a deployed configuration where the one or more needles pierce into and through the tissue positioned within the elongated channel such that the needles pass one or more lengths of suture through the tissue in an arcuate path, wherein each of the one or more lengths of suture defines a looped segment formed upon a portion of each of the one or more needles such that each looped segment is passed through the tissue;
    aligning each looped segment along a locking channel within the elongated channel when the one or more needles are in the deployed configuration and where the one or more needles are received at an angle relative to the locking channel; and,
    cinching each looped segment within the locking channel such that the one or more lengths of suture passed through the tissue are secured.

18. The method of claim 17 wherein introducing a shaft comprises introducing the shaft through a single incision along a posterior region of a leg.

19. The method of claim 17 wherein positioning a section comprises placing a segment of the tissue within elongated channel.

20. The method of claim 17 wherein actuating one or more needles comprises actuating a handle attached to a proximal end of the shaft.

21. The method of claim 17 wherein actuating one or more needles comprises actuating the one or more needles simultaneously.

22. The method of claim 17 wherein actuating one or more needles comprises actuating the one or more needles sequentially.

23. The method of claim 17 further comprising translating the shaft such that the needles are secured through the tissue while actuating.

24. The method of claim 17 wherein cinching comprises translating a cinching member through the locking channel such that each of the lengths of suture are secured.

25. The method of claim 17 further comprising retracting the one or more needles and withdrawing the shaft from an incision.

26. The method of claim 25 further comprising re-introducing the shaft into the incision in proximity to a second portion of the ruptured or torn tissue.

27. The method of claim 26 further comprising approximating the first and second portions of the tissue towards one another.

28. The method of claim 27 further comprising securing the first and second portions of the tissue to one another.

29. The method of claim 17 wherein introducing a shaft comprises introducing the shaft in proximity to a ruptured or torn tendon.

30. The method of claim 17 wherein actuating one or more needles comprises passing each looped segment into and through the tissue via the needle portion.

31. The method of claim 17 wherein cinching each looped segment comprises actuating a cinching member in a direction transverse to each looped segment.

32. The method of claim 17 wherein cinching each looped segment comprises actuating a cinching member in a direction parallel with the elongated channel.

\* \* \* \* \*